US00PP19904P2

(12) United States Plant Patent
Klemm

(10) Patent No.: US PP19,904 P2
(45) Date of Patent: Apr. 14, 2009

(54) *STREPTOCARPUS* PLANT NAMED 'KLEST07337'

(50) Latin Name: *Streptocarpus saxorum*
Varietal Denomination: KLEST07337

(75) Inventor: Nils Klemm, Stuttgart (DE)

(73) Assignee: Klemm + Sohn GmbH + Co. KG, Stuttgart (DE)

( * ) Notice: Subject to any disclaimer, the term of this patent is extended or adjusted under 35 U.S.C. 154(b) by 0 days.

(21) Appl. No.: 12/005,099

(22) Filed: Dec. 20, 2007

(51) Int. Cl.
*A01H 5/00* (2006.01)

(52) U.S. Cl. ..... Plt./333

(58) Field of Classification Search ..... Plt./333
See application file for complete search history.

*Primary Examiner*—Annette H Para
*Assistant Examiner*—June Hwu

(74) *Attorney, Agent, or Firm*—C. A. Whealy

(57) ABSTRACT

A new and distinct cultivar of *Streptocarpus* plant named 'KLEST07337', characterized by its outwardly spreading to trailing growth habit; freely branching habit; freely flowering habit; double red purple-colored flowers; and good garden performance.

1 Drawing Sheet

Botanical designation: *Streptocarpus saxorum.*
Cultivar denomination: 'KLEST07337'.

BACKGROUND OF THE INVENTION

The present invention relates to a new and distinct cultivar of *Streptocarpus,* botanically known as *Streptocarpus saxorum* and hereinafter referred to by the name 'KLEST07337'.

The new *Streptocarpus* is a product of a planned breeding program conducted by the Inventor in Stuttgart, Germany. The objective of the breeding program is to create new compact *Streptocarpus* cultivars with large attractive flowers.

The new *Streptocarpus* originated from a cross-pollination made by the Inventor in 2003 in Stuttgart, Germany of an unnamed proprietary selection of *Streptocarpus saxorum,* not patented, as the female, or seed, parent with a proprietary selection of *Streptocarpus saxorum* identified as code number A 014, not patented, as the male, or pollen, parent. The new *Streptocarpus* was discovered and selected by the Inventor as a single flowering plant within the progeny of the stated cross-pollination in a controlled environment in Stuttgart, Germany in 2004.

Asexual reproduction of the new *Streptocarpus* by cuttings in a controlled environment in Stuttgart, Germany since June, 2004, has shown that the unique features of this new *Streptocarpus* are stable and reproduced true to type in successive generations.

SUMMARY OF THE INVENTION

The cultivar KLEST07337 has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'KLEST07337'. These characteristics in combination distinguish 'KLEST07337' as a new and distinct cultivar of *Streptocarpus:*

1. Upright and mounding growth habit.
2. Freely branching habit.
3. Relatively small leaves.
4. Early and freely flowering habit.
5. Dark violet-colored flowers.

Plants of the new *Streptocarpus* can be compared to plants of the female parent selection. Plants of the new *Streptocarpus* differ from plants of the female parent selection in the following characteristics:

1. Plants of the new *Streptocarpus* are more compact than plants of the female parent selection.
2. Plants of the new *Streptocarpus* and the female parent selection differ in flower color as plants of the female parent selection have lighter violet-colored flowers.

Plants of the new *Streptocarpus* can be compared to plants of the male parent selection. Plants of the new *Streptocarpus* differ from plants of the male parent selection in the following characteristics:

1. Plants of the new *Streptocarpus* have smaller flowers than plants of the male parent selection.
2. Plants of the new *Streptocarpus* and the male parent selection differ in flower color as plants of the male parent selection have lighter violet-colored flowers.

Plants of the new *Streptocarpus* can be compared to plants of the *Streptocarpus* cultivar Butterfly, not patented. In side-by-side comparisons conducted in Stuttgart, Germany, plants of the new *Streptocarpus* differed from plants of the cultivar Butterfly in the following characteristics:

1. Plants of the new *Streptocarpus* were less vigorous than plants of the cultivar Butterfly.
2. Plants of the new *Streptocarpus* had smaller leaves than plants of the cultivar Butterfly.
3. Plants of the new *Streptocarpus* had smaller flowers than plants of the cultivar Butterfly.

4. Plants of the new *Streptocarpus* and the cultivar Butterfly differed in flower color as plants of the cultivar Butterfly had lighter violet-colored flowers.

BRIEF DESCRIPTION OF THE PHOTOGRAPH

The accompanying colored photograph illustrates the overall appearance of the new *Streptocarpus,* showing the colors as true as it is reasonably possible to obtain in colored reproductions of this type. Colors in the photograph may differ slightly from the color values cited in the detailed botanical description which accurately describe the colors of the new *Streptocarpus*. The photograph is a close-up view of typical leaves and flowers of 'KLEST07337'.

DETAILED BOTANICAL DESCRIPTION

The aforementioned photograph and following observations, measurements and values describe plants grown in Stuttgart, Germany, under commercial practice during the spring in a glass-covered greenhouse with day temperatures ranging from 15° C. to 20° C., night temperatures ranging from 12° C. to 15° C. and maximum light levels of 50,000 lux. Plants were pinched one time. Rooted young plants had been growing for about three months when the photograph and description were taken. Plants used for the description were grown in 10-cm containers. In the following description, color references are made to The Royal Horticultural Society Colour Chart, 2001 Edition, except where general terms of ordinary dictionary significance are used.

Botanical classification: *Streptocarpus saxorum* cultivar KLEST07337.

Parentage:

*Female, or seed, parent.*—Unnamed proprietary selection of *Streptocarpus saxorum* not patented.

*Male, or pollen, parent.*—Proprietary selection of *Streptocarpus saxorum* identified as code number A 014, not patented.

Propagation:

*Type.*—By cuttings.

*Time to initiate roots, summer.*—About 12 days at temperatures of 20° C.

*Time to initiate roots, winter.*—About 15 days at temperatures of 20° C.

*Time to produce a rooted young plant, summer.*—About 17 days at temperatures of 20° C.

*Time to produce a rooted young plant, winter.*—About 21 days at temperatures of 20° C.

*Root description.*—Fine, fibrous; grey in color.

*Rooting habit.*—Freely branching.

Plant description:

*Plant and growth habit.*—Upright and mounding growth habit. Freely branching habit with about four to five lateral branches; low vigor.

*Plant height.*—About 10 cm to 15 cm.

*Plant diameter.*—About 15 cm to 20 cm.

Lateral branch description:

*Length.*—About 10 cm.

*Diameter.*—About 2 mm to 4 mm.

*Internode length.*—About 1 cm to 2 cm.

*Strength.*—Moderately strong.

*Texture.*—Slightly pubescent.

*Color.*—Close to 144A.

Foliage description:

*Arrangement.*—Opposite, simple.

*Length.*—About 2 cm to 4 cm.

*Width.*—About 1.5 cm to 3 cm.

*Shape.*—Elliptic.

*Apex.*—Acute.

*Base.*—Obtuse.

*Margin.*—Entire.

*Texture, upper and lower surfaces.*—Pubescent; leathery.

*Venation pattern.*—Pinnate.

*Color.*—Developing and fully expanded foliage, upper surface: 137A; venation, 137A. Developing and fully expanded foliage, lower surface: 139C; venation, 139C.

*Petiole length.*—About 1 cm.

*Petiole diameter.*—About 1 mm to 1.5 mm.

*Petiole texture, upper and lower surfaces.*—Velvety.

*Petiole color, upper surface.*—Close to 137A.

*Petiole color, lower surface.*—Close to 139C.

Flower description:

*Flower arrangement and habit.*—Single salverform flowers arranged on terminal and axillary racemes. Freely flowering habit with usually about two to five flowers per inflorescence and 30 to 40 flowers developing per plant. Flowers not persistent. Flowers face mostly outwardly.

*Fragrance.*—None detected.

*Natural flowering season.*—Plants flower continuously throughout the year in Germany; plants begin flowering about five to six weeks after planting.

*Flower longevity.*—Individual flowers last about two to three days on the plant.

*Flower diameter.*—About 2 cm to 2.5 cm.

*Flower length (height).*—About 3 cm to 4 cm.

*Corolla tube length.*—About 3.5 cm.

*Flower bud.*—Shape: Ovoid. Length: About 5 mm to 8 mm. Diameter: About 3 mm. Color: 83A.

*Petals.*—Arrangement: Five petals fused at the base. Length: About 2 cm to 3 cm. Width: About 1.5 cm to 2 cm. Shape: Reniform. Apex: Obtuse. Margin: Entire. Texture, upper and lower surfaces: Smooth, glabrous. Color: When opening and fully opened, upper surface: Between 90A and 83A; towards the base, close to 155D; color becoming closer to 90C with development. When opening and fully opened, lower surface: 83D.

*Sepals.*—Arrangement: One funnel-shaped calyx tube with five sepals fused at the base per flower. Length: About 3 mm to 4 mm. Width: About 1 mm. Shape: Lanceolate. Apex: Acute. Margin: Entire. Texture, upper and lower surfaces: Smooth, glabrous; satiny. Color, upper and lower surfaces: 200B.

*Peduncles.*—Length: About 10 cm to 15 cm. Diameter: About 1 mm. Angle: About 30° to 70° from vertical. Strength: Weak. Texture: Smooth, glabrous. Color: 187A.

*Pedicels.*—Length: About 2 cm to 3 cm. Diameter: About 1 mm. Angle: About 30° from peduncle axis. Strength: Weak. Texture: Smooth, glabrous. Color: 187A.

*Reproductive organs.*—Stamens: Quantity/arrangement: About three per flower. Anther shape: Elliptic. Anther length: About 1 mm. Anther color: 11D. Pollen amount: Moderate. Pollen color: 11B. Pistils: Quantity: One per flower. Pistil length: About 1 cm. Stigma shape: Reniform. Ovary color: 144B. Seed/fruit: Seed and fruit development have not been observed on plants of the new *Streptocarpus*.

Temperature tolerance: Plants of the new *Streptocarpus* have been observed to tolerate temperatures ranging from about 12° C. to about 35° C.

Pathogen/pest resistance: Plants of the new *Streptocarpus* have not been observed to be resistant to pathogens and pests common to *Streptocarpus*.

It is claimed:

1. A new and distinct *Streptocarpus* plant named 'KLEST07337' as illustrated and described.

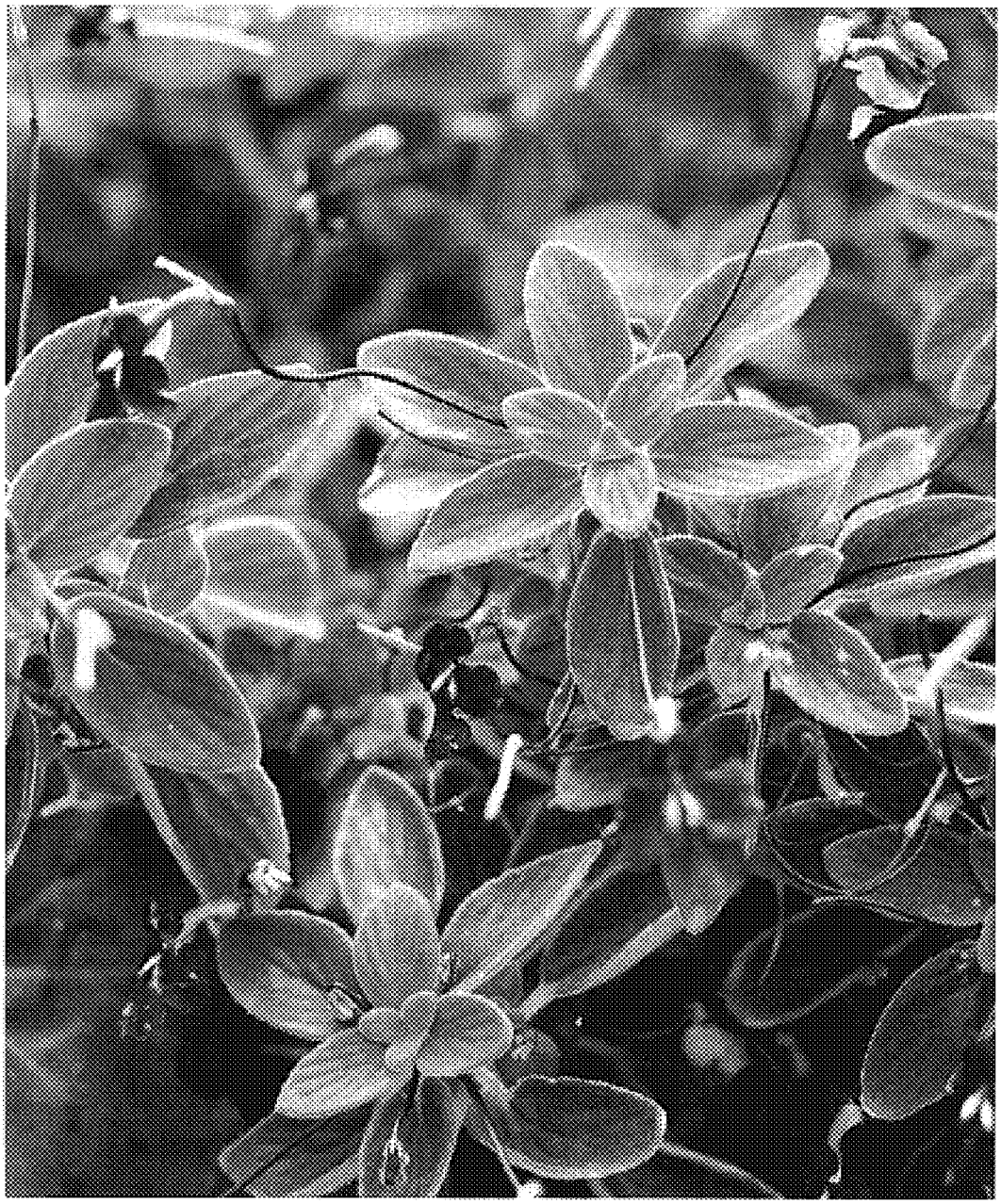

* * * * *